United States Patent
Rolfes et al.

(10) Patent No.: US 11,737,963 B2
(45) Date of Patent: *Aug. 29, 2023

(54) HAIR CONDITIONER COMPOSITION UTILIZING A HEAT STYLING RESPONSIVE FILM

(71) Applicant: KAO USA INC., Cincinnati, OH (US)

(72) Inventors: Michelle Rolfes, Amelia, OH (US); Adam Schrott, Hebron, KY (US)

(73) Assignee: Kao USA Inc., Cincinnati, OH (US)

( * ) Notice: Subject to any disclaimer, the term of this patent is extended or adjusted under 35 U.S.C. 154(b) by 23 days.

This patent is subject to a terminal disclaimer.

(21) Appl. No.: 17/514,290

(22) Filed: Oct. 29, 2021

(65) Prior Publication Data

US 2022/0047479 A1 Feb. 17, 2022

Related U.S. Application Data

(63) Continuation-in-part of application No. 15/878,890, filed on Jan. 24, 2018, now Pat. No. 11,191,715.

(51) Int. Cl.
| | |
|---|---|
| *A61Q 5/12* | (2006.01) |
| *A61K 8/41* | (2006.01) |
| *A61K 8/42* | (2006.01) |
| *A61K 8/92* | (2006.01) |
| *A61K 8/36* | (2006.01) |
| *A61K 8/34* | (2006.01) |

(52) U.S. Cl.
CPC .............. *A61K 8/416* (2013.01); *A61K 8/342* (2013.01); *A61K 8/36* (2013.01); *A61K 8/42* (2013.01); *A61K 8/922* (2013.01); *A61Q 5/12* (2013.01); *A61K 2800/596* (2013.01); *A61K 2800/805* (2013.01)

(58) Field of Classification Search
None
See application file for complete search history.

(56) References Cited

U.S. PATENT DOCUMENTS

| | | | |
|---|---|---|---|
| 6,528,046 B1 * | 3/2003 | Schmenger | A61K 8/87 424/70.11 |
| 7,906,107 B2 | 3/2011 | Maillefer et al. | |
| 11,191,715 B2 * | 12/2021 | Rolfes | A61Q 5/06 |
| 2013/0142748 A1 | 6/2013 | Tamura et al. | |
| 2015/0007849 A1 * | 1/2015 | Cajan | A46B 15/0091 424/47 |
| 2016/0331657 A1 | 11/2016 | Lyons et al. | |
| 2017/0007518 A1 * | 1/2017 | Everaert | A61Q 5/12 |
| 2019/0224108 A1 | 7/2019 | Rolfes et al. | |
| 2021/0369579 A1 | 12/2021 | Liang et al. | |

FOREIGN PATENT DOCUMENTS

| | | | | |
|---|---|---|---|---|
| WO | WO-2015036051 A1 * | 3/2015 | ............ | A61K 8/365 |
| WO | WO 2021/134118 A1 | 7/2021 | | |
| WO | WO 2021/151177 A1 | 8/2021 | | |
| WO | WO 2022/046595 A1 | 3/2022 | | |

OTHER PUBLICATIONS

Internal Applicant document showing the dates of commercialization for the subject hair conditioner composition.

* cited by examiner

*Primary Examiner* — Jyothsna A Venkat
(74) *Attorney, Agent, or Firm* — Frost Brown Todd LLP

(57) ABSTRACT

A hair care composition having a combination of a mixture of alkyl amine cationic surfactants, high melting point wax to provide a hydrophobic film (frizz resistance) and thermopliable film (heat styling response), along with a lightweight conditioner, to produce a hair care composition that is far less susceptible to buildup than traditional products currently marketed.

1 Claim, No Drawings

HAIR CONDITIONER COMPOSITION UTILIZING A HEAT STYLING RESPONSIVE FILM

PRIORITY

This application is a continuation-in-part of U.S. application Ser. No. 15/878,890, filed on Jan. 24, 2018, which is herein incorporated by reference in its entirety and claims priority to said application.

FIELD OF THE INVENTION

The present invention provides the qualities expected from a hair conditioner coupled with a unique thermo-pliable film that responds to heat from common consumer hair styling appliances.

BACKGROUND

Consumers desire sufficient detangling, moisturization, and frizz control from hair conditioners that aid in achieving their desired style.

In washing, drying, and styling one's hair several end results are desired. Firstly, and most obviously, one desires that the hair be thoroughly cleaned. Most desirable is a hair care process which maintains the look and feel of clean hair between hair washings. Also in the cleaning and styling process, one desires hair conditioning providing ease of combing, relief from static electricity, manageability, and soft hair feel. Generally, these benefits are provided by a separate hair conditioning product.

Finally, one desires a hair care process or product that provides hair styling benefits, especially hair style achievement and hold. The desire to have hair retain a particular shape is widely held. Such style retention is generally accomplished by either of two routes: permanent chemical alteration or temporary alteration of hair style/shape. A temporary alteration is one which can be removed by water or by shampooing. Temporary style alteration has generally been accomplished by means of the application of a third separate composition or compositions to dampened hair after shampooing and/or conditioning. The materials used to provide setting benefits have generally been resins or gums and have been applied in the form of mousses, gels, lotions, or sprays. This approach presents several significant drawbacks to the user. It requires a separate step following shampooing and conditioning to apply the styling composition. In addition, since the style hold is provided by resin materials which set-up on the hair, the hair tends to feel sticky or stiff after application and it is difficult to restyle the hair without further application of the styling composition.

Many modern hair styles require the use of heat tools to dry and style hair to reach a desired look. However, often consumers are frustrated by the use of such tools as they produce unmanageable hair and increase the occurrence of undesirable features such as frizz and flyaways.

It has now been discovered that two separate hair care benefits, i.e., conditioning and styling, can be provided by a single hair care product. In addition, the present invention provides for the ability to use low temperature heat of common consumer hair appliances to produce immediate manageability of hair, wherein the average maximum temperature is less than 110° C.

BRIEF SUMMARY

Existing rinse-off products attempt to provide improved styling with consumer hair appliances through the application of high concentration of quaternary ammonium cationic surfactant compounds that can build up on hair, leaving it feeling greasy and weighed down. Subsequent uses of the conditioner increase static-induced frizz due to the bulky nature of the compounds and increased static repulsion between fibers as a result. High viscosity dimethicone/dimethiconols/amodimethicones can also feel greasy and leave hair feeling weighed down.

Existing leave-on products attempt to provide protection from heat and frizz through the application of high volatility silicones (phenyltrimethicone/caprylyl trimethicone/cyclohexasiloxane/cyclopentasiloxane) that may provide only temporary shine during styling. High viscosity dimethicone/dimethiconols/amodimethicones that are used for heat protection may also leave the hair greasy and weighed down.

This technology relates to a hair care composition comprising a high melting point waxy material to provide a hydrophobic and thermo-pliable film along with a lightweight conditioner, to produce a hair care composition that is far less susceptible to buildup than products currently marketed. The inclusion of a neutralizing acid, e.g., glyoxylic acid, acts to control the deposition of the thermos-pliable film to minimize unacceptable buildup on hair.

DETAILED DESCRIPTION

The present invention provides the qualities expected from a conditioner coupled with a unique thermo-pliable film that responds to heat generated by common consumer hair styling appliances. The composition may be applied to wet hair as a rinse off product and/or applied to damp or dry hair as a leave-on product.

This thermo-pliable hair care and styling composition comprises an alkyl amine cationic surfactant having a molecular weight from about 400 g/mol to about 500 g/mol. The amount of alkyl amine cationic surfactant present in the composition may range from about 0.1% to about 7% by weight of, or from about 0.1 to about 5% by weight, or from about 1% to about 3% by weight, or from about 2% to about 5% by weight. The alkyl amine cationic surfactant may be selected from behentrimonium chloride, behenamidopropyl dimethylamine, behentrimonium methosulfate, and mixtures thereof.

The composition may also contain from about 0.1% to 15% long chain fatty alcohols. Examples of such alcohols include behenyl alcohol, cetyl alcohol, stearyl alcohol, cetearyl alcohol, arachidyl alcohol, and mixtures thereof. The melting point of long chain fatty alcohol is from about 45° C. to about 80° C.

The composition may also contain a high melting point waxy material, having a melting point from about 65° C. to about 90° C., present in amounts ranging from about 0.1% to about 5% (by weight); 1% to about 3% (by weight); or from about 0.75% to about 1.5% (by weight). Specifically, the high melting point waxy material may be selected from natural waxes, hydrocarbon waxes, and mixtures thereof, for instance, and not limited to, paraffin wax, ozokerite wax, ceresine wax, carnauba wax, rice bran wax, and mixtures thereof. Also, the composition may also contain from about 0.1 to 3% of neutralizing C2 to C4 carboxylic acid with an individual pKa from about 3.1 to about 4.6. Such neutralizing carboxylic acids may be selected from oxalic acid, glycolic acid, lactic acid, succinic acid, malic acid, glyoxylic acid and mixtures thereof. A suitable hair care carrier may also be utilized, wherein the point at which the composition first begins to melt is less than or equal to any solid materials utilized in the composition. The ratio of the cationic surfactant to the long chain fatty alcohol is from about 1:4 to about 1:1.

The onset of melting point (first detectable melting point) for the overall composition is from about 46° C. to about 90° C.

Generally, for this hair care composition, crystallization point(s) of the composition are usually not less than about 46° C.

The hair composition may be in a form chosen from a liquid, a solution, an emulsion, a cream, a gel, a paste, a mousse, a foam, or any other form that is suitable for application to keratin fibers.

Examples of the hair care composition include but are not limited to the following:

added as an emollient/hair conditioner. Benzyl alcohol functions as a preservative, and sodium hydroxide serves as a pH adjuster as well. Hydrolyzed keratin is also added for hair conditioning.

As shown in Example 11, behentrimonium chloride and behenamidopropyl dimethylamine function together as a mixture of alkyl amine cationic surfactants/emulsifying agents. The mixture is present in an amount of greater than 2% to 5% by weight of the composition, with each alkyl amine cationic surfactant present in an amount of at least 1.0% by weight of the composition. In one instance, as shown in the Table above, behenamidopropyl dimethylamine is present at an amount lower than that of behentrimonium chloride. In a specific instance, behenamidodipropyl

|  | Example #1 | Example #2 | Example #3 | Example #4 | Example #5 | Example #6 | Example #7 | Example #8 | Example #9 | Example #10 | Example #11 |
|---|---|---|---|---|---|---|---|---|---|---|---|
| Deionized Water | QS | QS | QS | QS | QS | QS | QS | QS | QS | QS | 87.875 |
| Behentrimonium Chloride | 4 |  |  | 3 | 1.71 |  |  |  | 1.5 |  | 1.5 |
| Behenamidopropyl Dimethylamine |  | 4 |  |  |  | 2.14 |  | 3 | 1.5 |  | 1.0 |
| Behentrimonium Methosulfate |  |  | 4 |  |  |  | 2.57 |  |  | 1.67 |  |
| Behenyl Alcohol |  |  | 1 | 0.5 |  |  | 0.25 | 0.1 |  |  |  |
| Cetyl Alcohol |  | 2 | 1 | 1 | 1 |  | 0.25 |  |  | 3 |  |
| Stearyl Alcohol |  | 2 | 2 | 1 | 1 |  |  |  |  | 3 |  |
| Cetearyl Alcohol | 4 |  |  | 1 |  | 2 | 3 | 3 | 5 |  | 4.5 |
| Arachidyl Alcohol |  |  |  | 0.5 |  | s |  | 0.1 |  |  |  |
| Paraffin Wax | 3 | 0.25 |  |  |  |  |  | 0.67 |  |  |  |
| Ozokerite Wax | 0.25 |  |  | 0.25 | 3 | 1 |  |  |  |  |  |
| Ceresine Wax |  | 3 |  |  |  |  | 0.5 |  |  |  |  |
| Carnauba Wax |  |  | 0.25 | 3 |  |  |  |  |  | 0.75 | 1.2 |
| Rice Bran Wax |  |  | 3 |  | 0.25 |  |  |  |  | 0.25 |  |
| bis-diisopropanolamino-PG-propyl dimethicone/bis-isobutyl PEG-14 copolymer, and polysorbate 20, and butyloctanol (trade name DOWSIL CE-8411 Smooth Plus Emulsion) |  |  |  |  |  |  |  |  |  |  | 1.0 |
| Dimethicone (5000cst) |  |  |  |  |  |  |  |  |  |  | 0.75 |
| Glyoxylic acid |  |  |  |  |  |  |  |  |  |  | 0.5 |
| Benzoic acid |  |  |  |  |  |  |  |  |  |  | 0.35 |
| Isopropyl palmitate |  |  |  |  |  |  |  |  |  |  | 0.3 |
| Benzyl alcohol NF |  |  |  |  |  |  |  |  |  |  | 0.25 |
| Sodium hydroxide (50%) |  |  |  |  |  |  |  |  |  |  | 0.055 |
| Cocos Nucifera (Coconut) oil |  |  |  |  |  |  |  |  |  |  | 0.010 |
| Hydroluzed keratin |  |  |  |  |  |  |  |  |  |  | 0.010 |
| pH Adjuster | QS | QS | QS | QS | QS | QS | QS | QS | QS | QS | QS |
| Fragrance | QS | QS | QS | QS | QS | QS | QS | QS | QS | QS | 0.70 |
| Preservative | QS | QS | QS | QS | QS | QS | QS | QS | QS | QS | QS |

The ingredients, particularly for example 11 in the Table, may be generally used in such hair care formulations. The de-ionized water serves as a vehicle/solvent for the composition. The cetearyl alcohol serves as a thickening agent. The copernicia cerifera (carnuba) wax is added for hair conditioning. The bis-diisopropanolamino-PG-propyl dimethicone/bis-isobutyl PEG-14 copolymer, and polysorbate 20, and butyloctanol (tradename DOW SIL CE-8411 Smooth Plus Emulsion) is also used for hair conditioning. Dimethicone is added for hair conditioning as well. Glyoxylic acid serves as a pH adjuster/neutralizing agent, and benzoic acid serves as a pH adjuster/preservative. Isopropyl palmitate is dimethylamine is present at 1.0% by weight of the composition, and behentrimonium chloride is present at 1.5% by weight of the composition.

Both alkyl amine cationic surfactants have a molecular weight ranging from 400 g/mol to 500 g/mol. Behentrimonium chloride has a molecular weight less than that of behenamidopropyl dimethylamine. For instance, behentrimonium chloride has a molecular weight of 403 g/mol, and behenamidopropyl dimethylamine has a molecular weight of 424 g/mol.

What is claimed:

1. A hair care composition, wherein the hair care composition is formulated as a leave-in hair care composition, the hair care composition consisting of:

a) about 1.5% by weight of behentrimonium chloride;
b) about 1.0% by weight of behenamidopropyl dimethylamine;
c) about 4.5% by weight of cetearyl alcohol;
d) about 1.2% by weight of carnauba wax;
e) about 1.0% by weight of bis-diisopropanolamino-PG-propyl dimethicone/bis-isobutyl PEG-14 copolymer, and polysorbate 20, and butyloctanol;
f) about 0.75% by weight of dimethicone;
g) about 0.5% by weight of glyoxylic acid;
h) about 0.35% by weight of benzoic acid;
i) about 0.3% by weight of isoproypyl palmitate;
j) about 0.25% by weight of benzyl alcohol;
k) about 0.055% by weight of sodium hydroxide;
l) about 0.010% by weight of coconut oil;
m) about 0.010% by weight of hydrolyzed keratin; and
n) deionized water, pH adjuster, fragrance, and preservative to bring the composition to 100% by weight.

* * * * *